United States Patent
Ghisoni

(10) Patent No.: US 10,837,030 B2
(45) Date of Patent: Nov. 17, 2020

(54) YEAST PROPAGATION SIMULTANEOUS WITH SACCHARIFICATION

(71) Applicants: LESAFFRE ET COMPAGNIE, Paris (FR); AGRO INDUSTRIE RECHERCHES ET DEVELOPPEMENTS A.R.D., Pomacle (FR); INSTITUT NATIONAL DE LA RECHERCHE AGRONOMIQUE INRA, Paris (FR)

(72) Inventor: Flora Ghisoni, Saint Jeannet (FR)

(73) Assignees: LESAFFRE ET COMPAGNIE, Paris (FR); AGRO INDUSTRIE RECHERCHES ET DEVELOPPEMENTS A.R.D., Pomacle (FR); INSTITUT NATIONAL DE LA RECHERCHE AGRONOMIQUE INRA, Paris (FR)

( * ) Notice: Subject to any disclaimer, the term of this patent is extended or adjusted under 35 U.S.C. 154(b) by 0 days.

(21) Appl. No.: 15/577,880

(22) PCT Filed: May 26, 2016

(86) PCT No.: PCT/FR2016/051237
§ 371 (c)(1),
(2) Date: Nov. 29, 2017

(87) PCT Pub. No.: WO2016/193576
PCT Pub. Date: Dec. 8, 2016

(65) Prior Publication Data
US 2018/0142268 A1 May 24, 2018

(30) Foreign Application Priority Data
May 29, 2015 (FR) ...................... 15 54902

(51) Int. Cl.
| | |
|---|---|
| *C12P 7/10* | (2006.01) |
| *C12N 1/16* | (2006.01) |
| *C12N 1/22* | (2006.01) |
| *C12N 9/42* | (2006.01) |
| *C12P 19/14* | (2006.01) |

(52) U.S. Cl.
CPC .................. *C12P 7/10* (2013.01); *C12N 1/16* (2013.01); *C12N 1/22* (2013.01); *C12N 9/2437* (2013.01); *C12P 19/14* (2013.01); *C12P 2201/00* (2013.01); *C12P 2203/00* (2013.01); *Y02E 50/16* (2013.01); *Y02E 50/343* (2013.01)

(58) Field of Classification Search
CPC ..................................... C12P 7/08; C12P 7/10
See application file for complete search history.

(56) References Cited

FOREIGN PATENT DOCUMENTS

| WO | 2009/155633 | 12/2009 |
|---|---|---|
| WO | 2014/072232 | 5/2014 |

OTHER PUBLICATIONS

A.S. Qureshi et al. "Cellulosic Ethanol Fermentation Using *Saccharomyces cerevisiae* Seeds Cultured by Pretreated Corn Stover Material", Appl. Biochem. Biotechnol. 175:3173-3183 (Year: 2015).*
J. Zhang et al. "Biodetoxification of toxins generated from lignocellulose pretreatment using a newly isolated fungus, *Amorphotheca resinae* ZN1, and the consequent ethanol fermentation", Biotechnology for Biofuels 3:26 pp. 1-15 (Year: 2010).*
International Search Report and Written Opinion of the International Searching Authority dated Aug. 1, 2016, which issued during prosecution of International Application No. PCT/FR2016/051237.
Cho, et al. "Novel SSF process for ethanol production from microcrystalline cellulose using the σ-integrated recombinant yeast, *Saccharomyces cerevisiae* L2612σGC" Journal of Microbiology and Biotechnology, Jun. 1999, 9(3):340-345.
Harner, et al. "Genetic improvement of native xylose-fermenting yeasts for ethanol production" Journal of Industrial Microbiology & Biotechnology, Jan. 2015, 42(1):1-20.
Harner, et al. "Mutants of the pentose-fermenting yeast *Pachysolen tannophilus* tolerant to hardwood spent sulfite liquor and acetic acid" Antonie Van Leeuwenhoek, Jan. 2014, 105(1):29-43.
Murthy, et al. "A simultaneous saccharification and fermentation model for dynamic growth environments" Bioprocess and Biosystems Engineering, Oct. 2011, 35(4):519-534.
Nielsen, et al. "Short-term adaptation during propagation improves the performance of xylose-fermenting *Saccharomyces cerevisiae* in simultaneous saccharification and co-fermentation" Biotechnology for Biofuels, Dec. 2015, 8(1):219.

* cited by examiner

*Primary Examiner* — Rebecca E Prouty
(74) *Attorney, Agent, or Firm* — Duane Morris LLP; Thomas J. Kowalski; Deborah L. Lu

(57) ABSTRACT

The invention relates to a method for propagating yeast, for use in the production of a fermentation product from lignocellulosic biomass, including the steps that consist of: a. providing a reactor; b. placing in contact in said reactor: a population of yeasts capable of metabolising pentoses and hexoses, with 0.2 to 2.0 g of yeast solids per kg of prepared complete medium, raw marc from the pretreatment of the lignocellulosic biomass, with a solids content (MS) of 8% to 15%, nutrients, and cellulases, with 5 to 15 mg of proteins per gram of MS; and c. incubating the mixture at a temperature of 25° C. to 38° C., preferably 28° C. to 33° C., in microaerobiosis, in which the saccharification of the raw marc and the growth of the yeast are carried out simultaneously.

11 Claims, 13 Drawing Sheets

YEAST PROPAGATION SIMULTANEOUS WITH SACCHARIFICATION

RELATED PATENT APPLICATIONS

The present patent application is filed pursuant to 35 U.S.C. § 371 as a U.S. National Phase Application of International Patent Application No. PCT/FR2016/051237, which was filed on May 26, 2016, claiming the benefit of priority to French patent application number FR 15 54902 filed on May 29, 2015. The International Application published as WO 2016/193576 on Dec. 8, 2016. The content of each of the aforementioned patent applications is incorporated herein by reference in its entirety.

The present invention relates to the field of yeasts used in the production of biofuels and of other green chemistry compounds, produced by a fermentation process.

The decrease in fossil energy stocks has led the industry to look for alternative solutions, using as much as possible renewable raw materials and less polluting processes. Among these solutions, mention will be made of the production of bioethanol from plant biomass, from biomass derived from plant waste or even from municipal waste. In order to be accepted, green versions of chemical compounds must be as efficient, or even more efficient, than the existing versions, and the processes for producing them must be economically competitive.

There are numerous applications: first-generation fuels, biodiesel or ethanol, derived from plant raw material such as sugar cane, beet, wheat, corn or vegetable oil, second-generation fuels, biodiesel, biokerosene, cellulose-based ethanol, derived from non-food plant biomass or from crop residues, and other heavy-chemistry or fine-chemistry products.

The raw material must be pretreated. Depending on its origin, the pre-treatment is mechanical (scraping, grinding, chopping, milling, pressure), thermal or chemical. The raw marc thus obtained is subjected to an extraction and/or to an enzymatic hydrolysis. This produces a fermentable substrate to which the fermenter microorganism is added. Finally, the fermentation product can be used for extracting products of interest, for example by distillation or extraction by means of a solvent. Various steps of this process constitute technological barriers and have been widely studied: pretreatment of the biomass to make it accessible to enzymes, definition of enzymatic mixtures for efficient hydrolysis of carbohydrate polymers or yet alcoholic fermentation of the various sugars obtained (pentoses, hexoses).

The step of alcoholic propagation of the yeast, which is the subject of the present invention, is not greatly described. In this respect, the present invention relates to a method for propagating yeasts, comprising the steps consisting in:
 a) providing a reactor
 b) placing in contact in said reactor:
  a population of yeasts capable of metabolizing pentoses and/or hexoses, in a proportion of from 0.2 to 2.0 g of yeast dry matter per kg of prepared complete medium,
  the raw pretreated marc composed of organic fibers, preferentially obtained from plant biomass, at a solids content (SC) of between 8% and 15%, preferentially of between 10% and 12%, even more preferentially of 10%,
  nutrients,
  a nitrogen source such as yeast extracts, urea, aqueous ammonia,
  cellulases, in a proportion of from 5 to 15 mg of enzymatic proteins per gram of SC,
 c) incubating the mixture at a temperature of between 25 and 38° C., preferably between 28 and 33° C., and in microaerobiosis,
wherein the saccharification of the raw marc and the growth of the yeasts are carried out simultaneously.

DEPOSITS

The Deposits with CNCM (Collection Nationale de Cultures de Microorganismes [French National Collection of Microorganism Cultures], Institut Pasteur, 25 rue du Docteur Roux, 75724 Paris Cedex 15) on May 24, 2012, under deposit accession number numbers I-4624, I-4625, I-4626 and I-4627 and the strain deposited on Jun. 26, 2013, under number I-4783 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

The sugar composition of the five substrates is the following:
 (1) Cellulose (glucose polymer) and solubilized hemicellulose (monomers and oligomers of hexoses and pentoses). Solid substrate.
 (2) Hydrolyzed cellulose and hydrolyzed hemicellulose (monomers and oligomers of hexoses and pentoses). Liquid substrate containing solids in suspension.
 (3) Cellulose (glucose polymer). Solid substrate.
 (4) Solubilized hemicellulose (monomers and oligomers of hexoses and pentoses). Liquid substrate.
 (5) Hydrolyzed cellulose (glucose). Liquid substrate containing solids in suspension.

Figure 2:
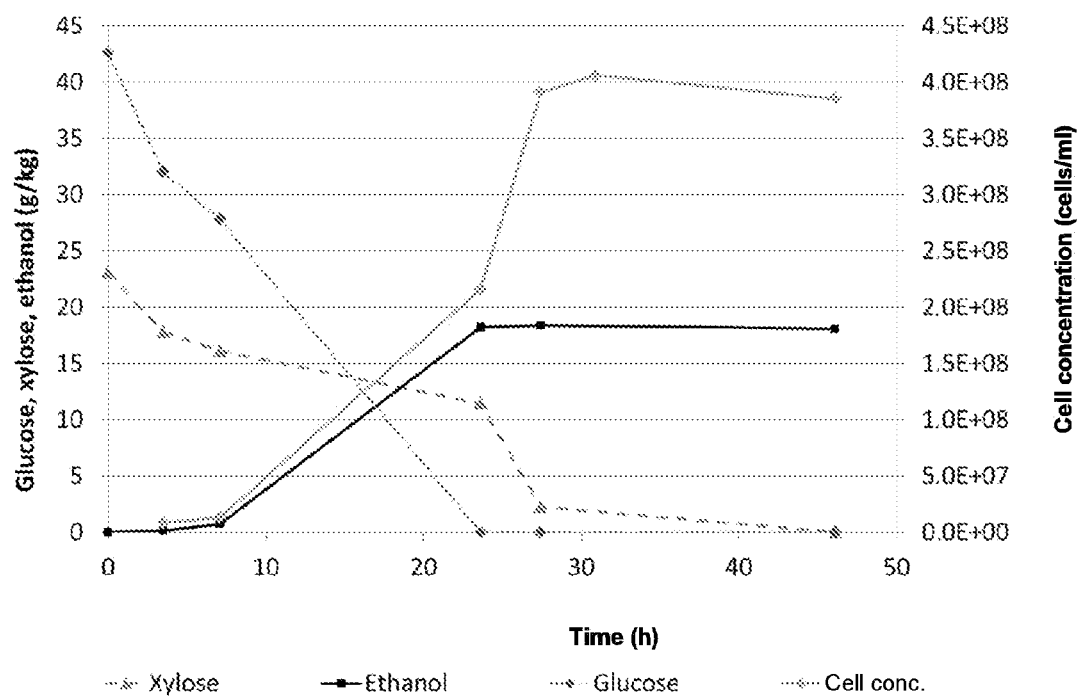

FIG. 2 illustrates the change in the concentrations of yeasts (in cells/ml), of substrates (C5 and C6 sugars) and of ethanol (in g/kg) during the propagation on lignocellulosic hydrolysate (or SHF for Separated Hydrolysis and Fermentation).

Figure 3:
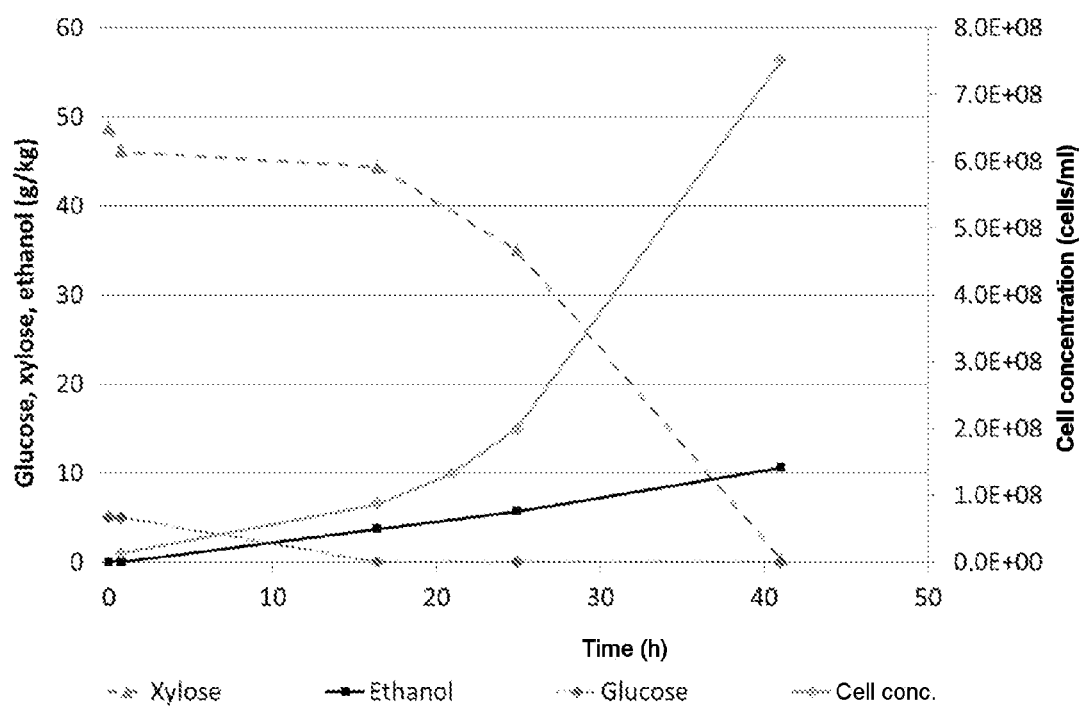

FIG. 3 illustrates the change in the concentrations of yeasts (in cells/ml), of substrates (C5 and C6 sugars) and of ethanol (in g/kg) during the propagation on C5 liquor.

Figure 4:
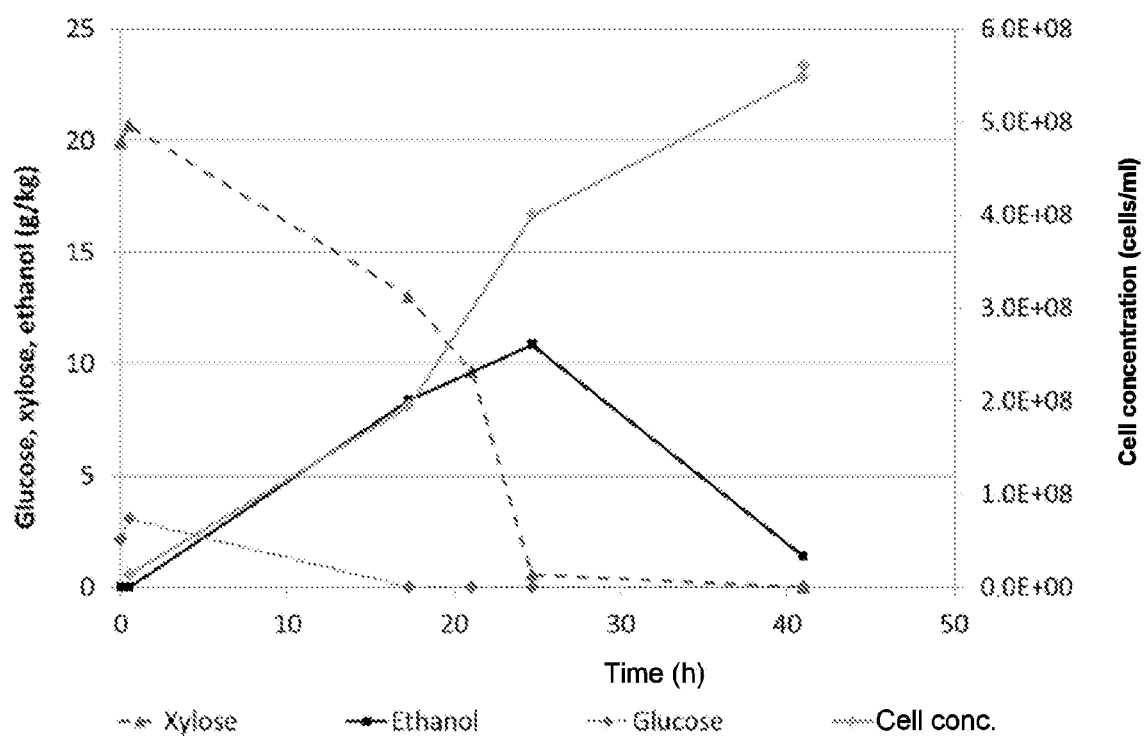

FIG. 4 illustrates the change in the concentrations of yeasts (in cells/ml), of substrates (C5 and C6 sugars) and of ethanol (in g/kg) during the SSP propagation (simultaneous saccharification and propagation) according to the invention, at 10% of SC and 10 mg of enzymatic proteins/g SC.

Figure 5:
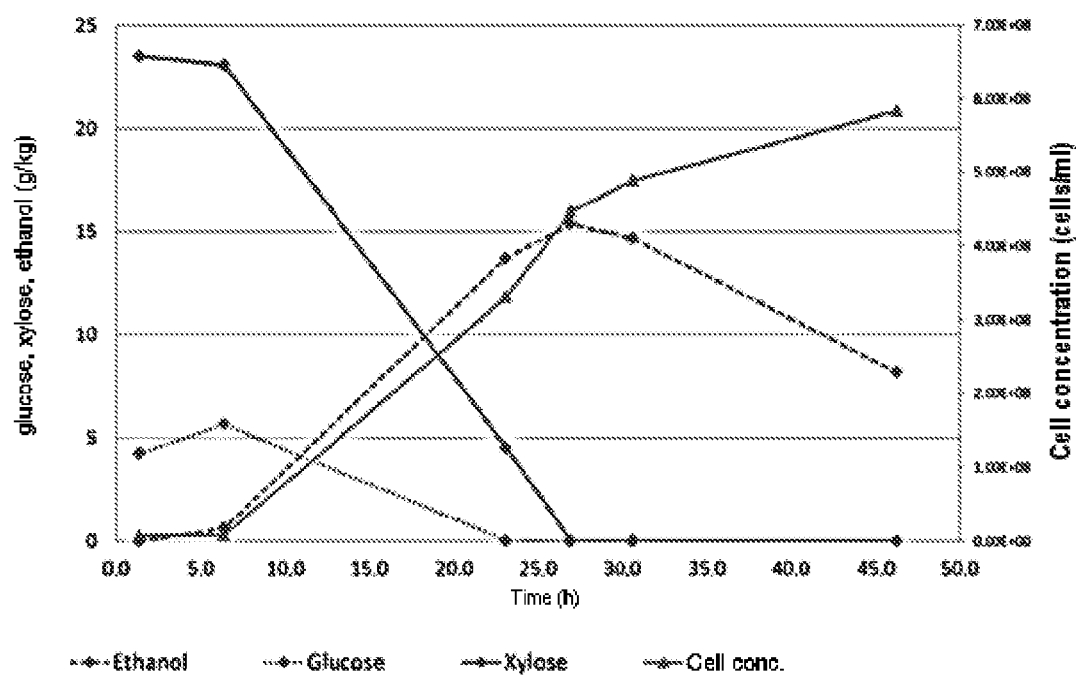

FIG. 5 illustrates the change in the concentrations of yeasts (in cells/ml), of substrates (C5 and C6 sugars) and of ethanol (in g/kg) during the SSP propagation according to the invention, at 12% of SC and 10 mg of enzymatic proteins/g SC.

Figure 6:
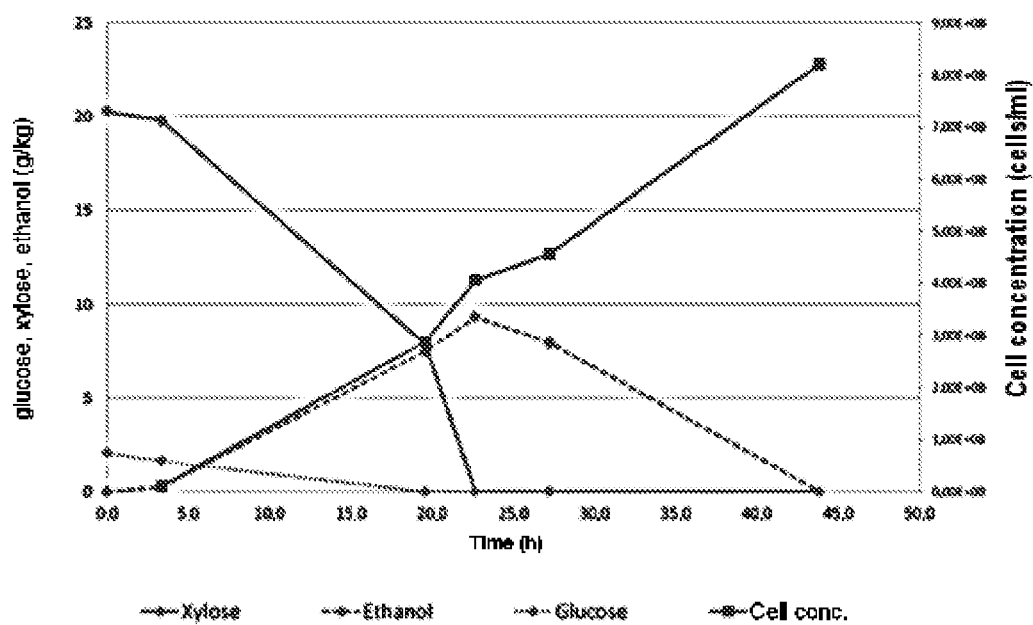

FIG. 6 illustrates the change in the concentrations of yeasts (in cells/ml), of substrates (C5 and C6 sugars) and of ethanol (in g/kg) during the SSP propagation according to the invention, at 10% of SC and 7 mg of enzymatic proteins/g SC.

Figure 7:
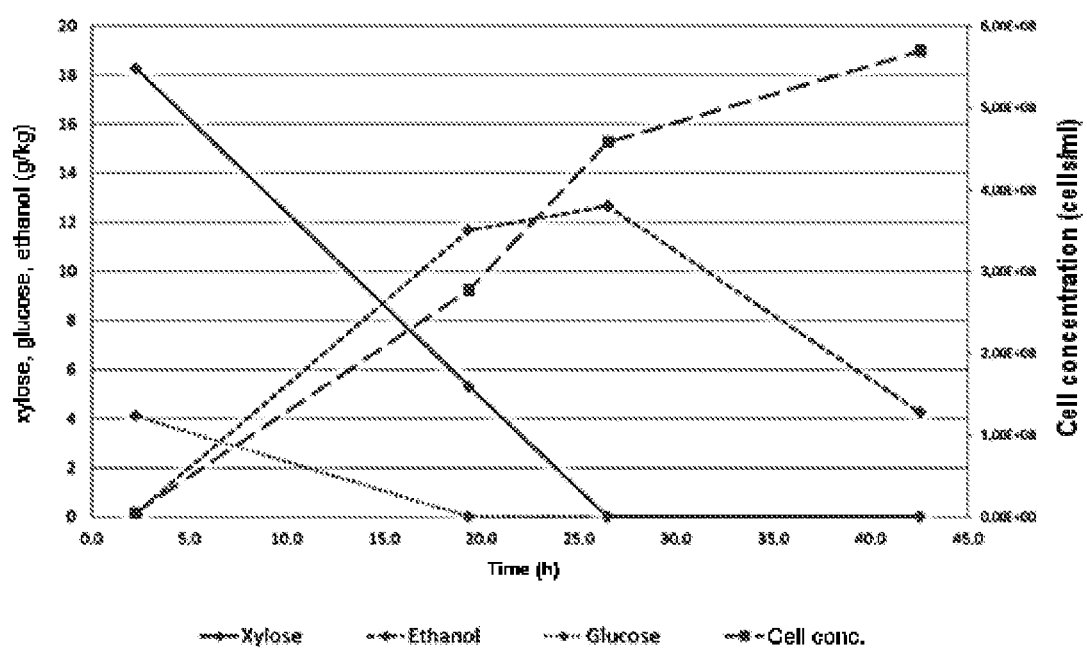

FIG. 7 illustrates the change in the concentrations of yeasts (in cells/ml), of substrates (C5 and C6 sugars) and of ethanol (in g/kg) during the SSP propagation according to the invention, at 32° C.

Figure 8:
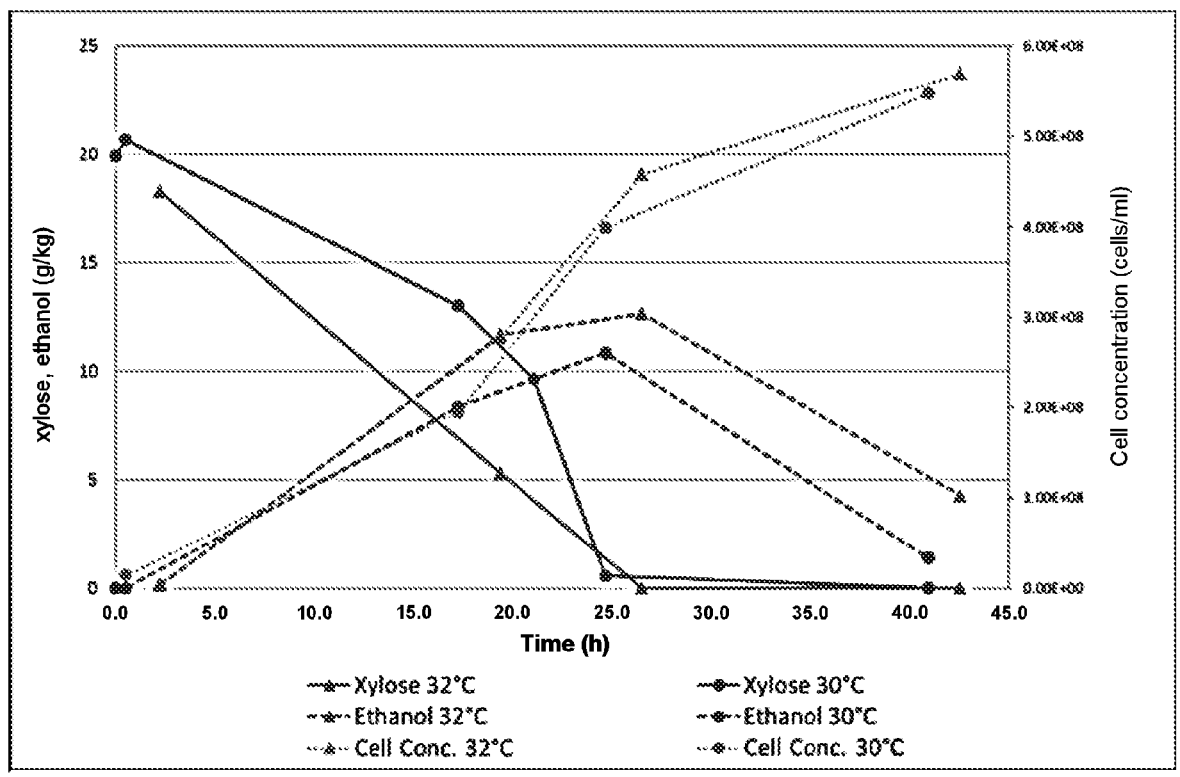

FIG. 8 compares the change in the concentrations of yeasts (in cells/ml), of substrates (C5 and C6 sugars) and of ethanol (in g/kg) during the SSP propagation according to the invention, at 30 and 32° C.

Figure 9:
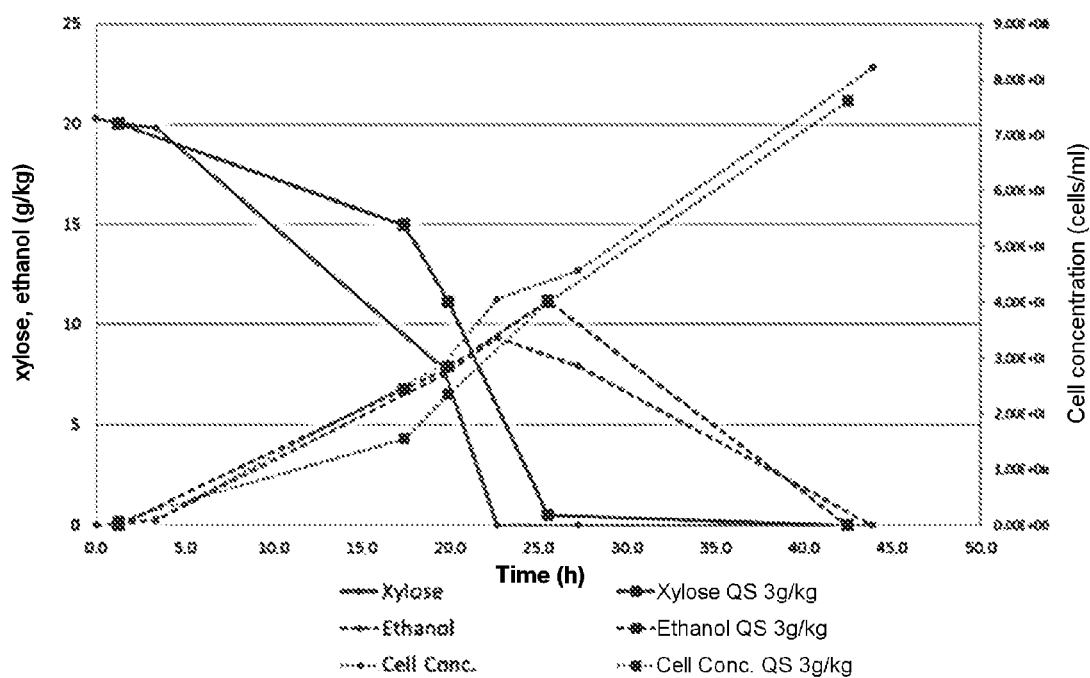

FIG. 9 illustrates the change in the concentrations of yeasts (in cells/ml), of substrates (C5 and C6 sugars) and of ethanol (in g/kg) during the SSP propagation according to the invention, at 10% of SC and 7 mg of enzymatic proteins/g SC, with and without addition of acetate.

Figure 10:
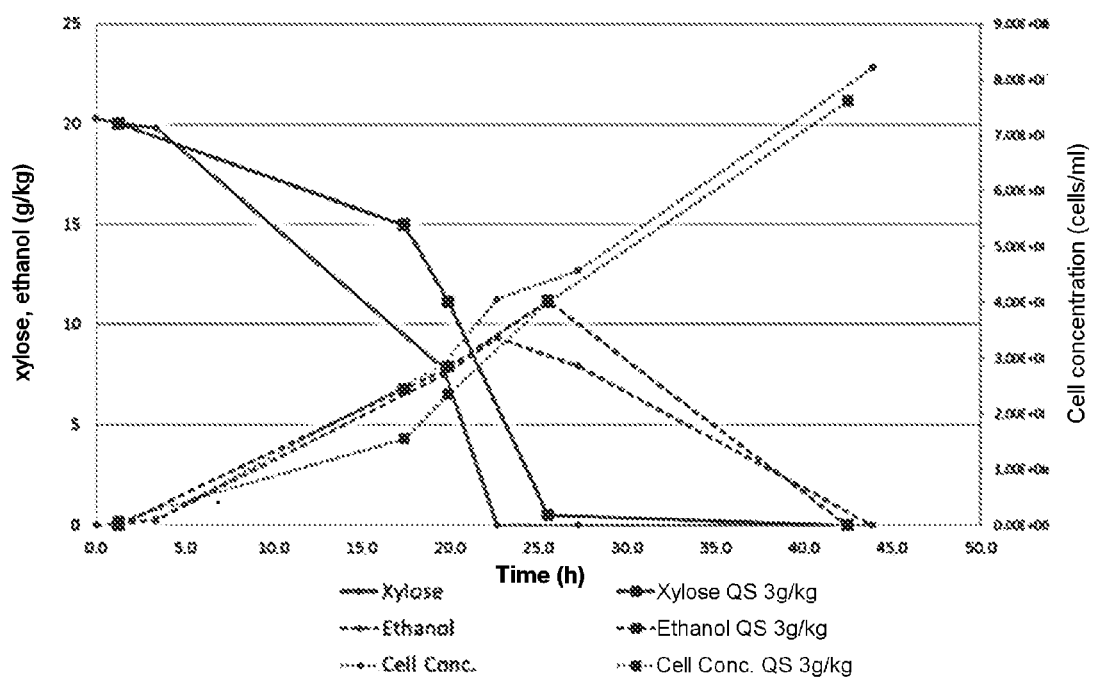

FIG. 10 illustrates the change in the concentrations of yeasts (in cells/ml), of substrates (C5 and C6 sugars) and of ethanol (in g/kg) during the SSP propagation according to the invention, at 10% of SC and 10 mg of enzymatic proteins/g SC, with and without addition of acetate.

Figure 11:
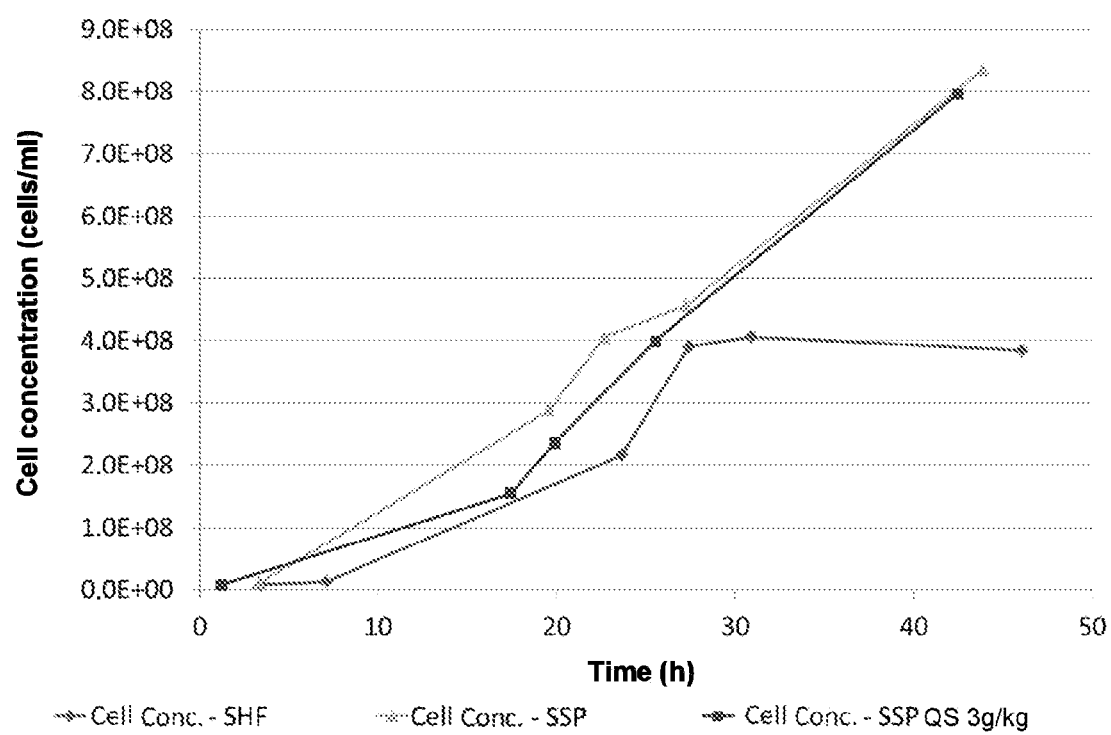

FIG. 11 compares the change in the concentrations of yeasts (in cells/ml) during the propagation on lignocellulosic hydrolysate (SHF) and the SSP propagation at 10% of SC and 7 mg of enzymatic proteins/g SC with and without addition of acetate.

Figure 12:
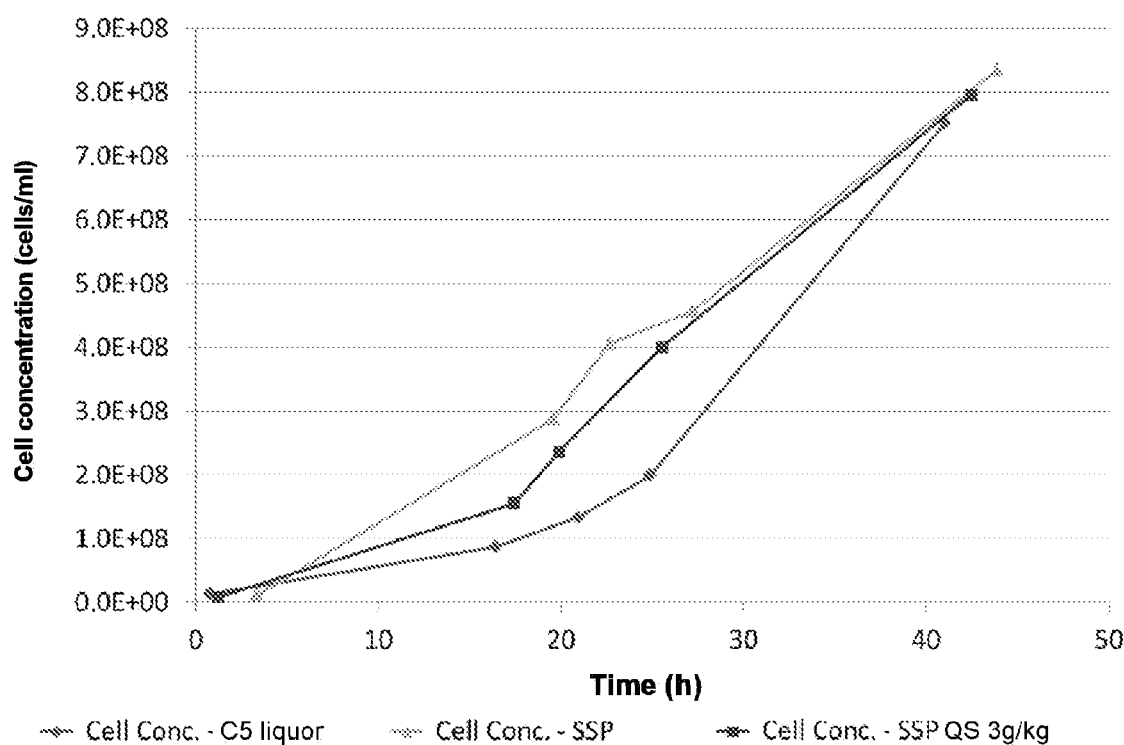

FIG. 12 compares the change in the concentrations of yeasts (in cells/ml) during the propagation on C5 liquor and the SSP propagation at 10% of SC and 7 mg of enzymatic proteins/g SC with and without addition of acetate.

Figure 13:
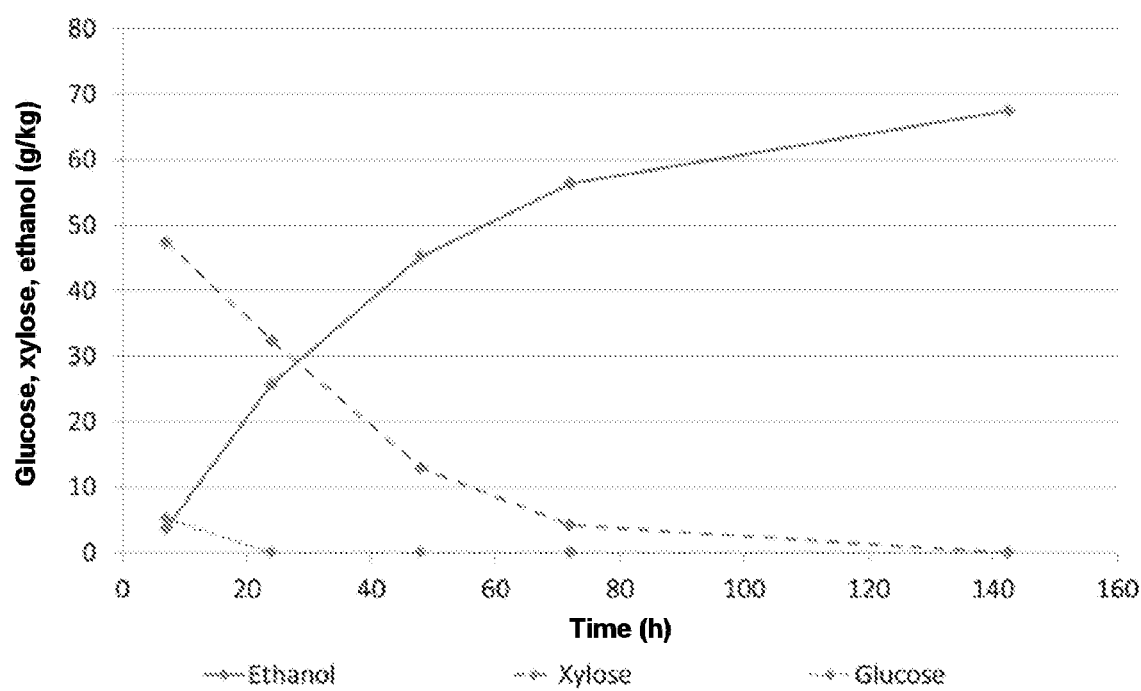

FIG. 13 illustrates the concentrations of sugars (C5 and C6) and of ethanol (in g/kg) during the SSCF fermentation on wheat straw with addition of acetate (qs 4 g/kg), inoculated with the I-4783 yeast propagated by SSP.

Figure 1:
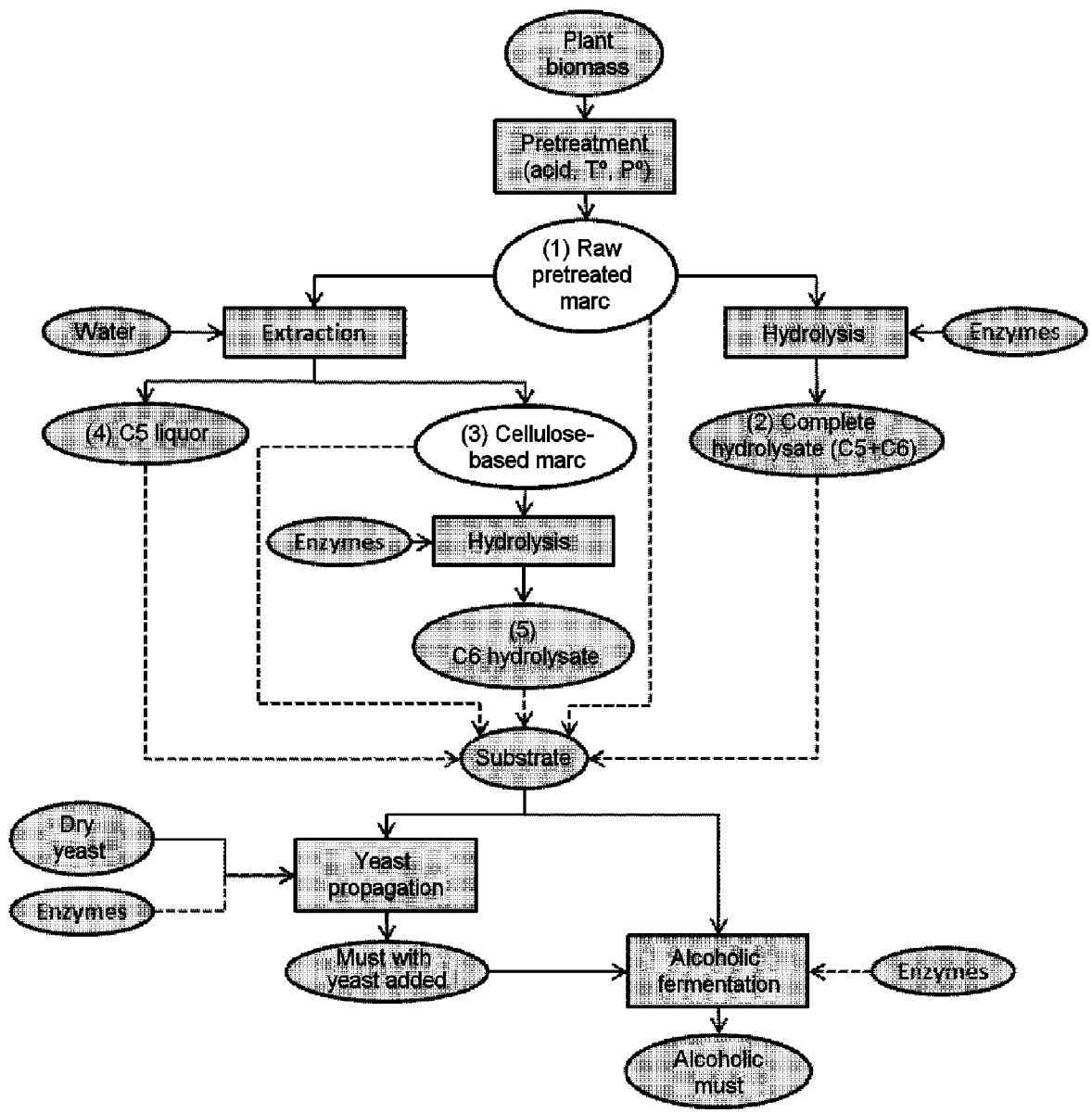
FIG. 1 presents a process for producing bioethanol, comprising the pretreatment, and the yeast propagation and alcoholic fermentation phases, while giving details of the various substrates capable of being generated by the process, said substrates being usable for the yeast propagation and ethanol production steps.

According to FIG. 1, the pretreated plant biomass can be used as substrate in yeast propagation and/or in alcoholic fermentation in five different forms:

The most widespread solution consists in carrying out a hydrolysis of the complete marc in the presence of cellulases, in order to obtain a liquid lignocellulosic hydrolysate (2) comprising a mixture of monomers of hexoses (C6) and of pentoses (C5), and also oligomers in small amount.

Another common substrate is hemicellulosic hydrolysate, also called "C5 liquor" (4), which corresponds to the soluble fraction of the substrate at the pretreatment output.

This extraction of the hemicellulosic hydrolysate (4) at the pretreatment output results in cellulose-rich cellulose-based marc (3) which can be hydrolyzed by virtue of cellulases in the same way as the complete marc. In this case, the cellulose-based hydrolysate obtained contains mainly glucose monomers (5).

This cellulose-rich cellulose-based marc (3), which is in solid form, can also be used without prior hydrolysis. In this case, the cellulases are added during fermentation and the hydrolysis of the cellulose and the consumption of glucose are carried out simultaneously.

Finally, the integration of the most thorough method consists in using the raw pretreated marc (1) as fermentation substrate without intermediate hydrolysis or separation step. In this case, the cellulases are added during fermentation and the hydrolysis of the cellulose is carried out simultaneously with the consumption of xylose and of hexoses. The latter option for the alcoholic fermentation step is known as simultaneous saccharification and co-fermentation (or SSCF) of the xylose and hexoses.

The propagation of the yeasts that will be used for the fermentation step involve different problems, in particular in terms of oxygen transfer.

It is conventionally carried out on C5 liquor (4). Thus, patent application US2014/0065700 mentions a propagation carried out on C5 liquor and application WO 2009/155633 indicates that the prior step of cellulose hydrolysis is essential.

The propagation is not dealt with a great deal in the scientific literature, and propagation carried out simultaneously with hydrolysis has never been described. The substrate used is either the soluble fraction at the pretreatment output (or C5 liquor), or a lignocellulosic hydrolysate obtained by prior hydrolysis of all of the pretreated plant. After propagation, the yeasts are used either for fermentation (with (SSF) or without saccharification), or for producing proteins of interest (Duarte et al., 2008; Applied Biochem Biotechnol, 148: 119-29; Meyer et al., 1992; Biotechnol Bioeng, 40 (3): 353-8; Holder et al., 1989; Biological Wastes, 28 (4): 239-46; Gonzalez-Valdes & Moo-Young, 1981; Biotechnology Letters, 3 (3): 143-8). Bellissimi & Richards (Bellissimi E, Richards C: Yeast propagation, in The alcohol textbook, a reference for the beverage, fuel and industrial alcohol industries, 5th edition, edited by Ingledew W M, Kelsall D R, Austin G D, Kluhspies C. Nottingham: University Press; 2009: 145-159) indicate that the method for producing industrial yeasts is an aerobic propagation, in which there is no production of alcohol and a maximum amount of cells is attained. This is because, for the yeast, the growth capacity over a long period of time and under strictly anaerobic conditions is limited.

One of the drawbacks of the raw pretreated marc before liquefaction or hydrolysis is its viscosity. For this reason, the liquefaction/solubilization or hydrolysis step is presumed to be essential. No document describes or suggests a simultaneous saccharification and propagation process.

Patent application WO 2011/56991 A1 describes a simultaneous saccharification and fermentation process, optionally with an aerated propagation, in parallel, in the hexose-rich liquefied medium that will be used for the fermentation. Patent application WO 2010/014817 A2 describes a process aimed at improving the quality and/or the quantity of the fermenter organism (yeast) during the fermentation phase. Patent application WO 2014/72232 A1 describes a process for aerobic propagation in a lignocellulosic hydrolysate (used as carbon source), in which the hydrolysate is added in "fed-batch" mode so as to obtain and to maintain a given pH in the reactor. Patent application US 2014/0273167 A1 describes an aerobic process for propagating yeasts, with stirring and aeration, on a hexose-rich substrate resulting from a hydrolysis. Patent application US 2014/0273166 A1 describes a process for propagating yeasts on a substrate resulting from the conversion of a plant biomass, said substrate being preferentially rich in pentoses. The yeasts subjected to propagation, in this case in point, are transformed yeasts capable of metabolizing pentoses.

The method of propagation on C5 liquor requires a complex step of extracting the liquid fraction from the pretreated marc. The method of propagation on C6-rich hydrolysate (or hydrolysate comprising a C5-C6 mixture) also requires a specific hydrolysis step. Such a step is expensive and time consuming. Thus, there remains a desire to improve the method to make a more integrated version, that retains satisfactory performance levels in terms of yield, productivity and multiplication rate.

The present invention provides a simultaneous saccharification and propagation method. Going against the prior art regarding the essential nature of a hydrolysis or extraction step prior to obtaining a substrate capable of yeast propagation, the applicant provides a method using the raw pretreated marc as yeast propagation substrate, without prior hydrolysis or separation steps. Said method combines the saccharification of the raw marc by cellulases and the growth of the yeasts using the available C5 sugar(s) and the C6 sugar(s) released by the enzymatic hydrolysis.

The simultaneous saccharification and propagation method according to the invention will subsequently be abbreviated to SSP (for Simultaneous Saccharification and Propagation).

An advantage of the propagation according to the invention is the reduction in time and cost due to the integration of the method by eliminating a step.

Another advantage of the invention is the limitation in terms of fermentable sugars due to the enzymatic hydrolysis carried out simultaneously which makes it possible to achieve a high biomass production yield without imposing a fed-batch protocol.

Another advantage of the invention is that the continually low glucose level promotes xylose consumption, which is usually inhibited in the presence of glucose.

Another advantage of the invention is that the high final biomass content (of about 17.4 g/kg) makes it possible to limit the size of the yeast propagation unit, and also the dilution of the fermentation must due to the inoculation which represents only 3% of the SSCF fermentation volume.

Another advantage of the invention is that the impact of the inhibitors present in the pretreated marc on the growth performance levels is significantly reduced.

Finally, another advantage of the invention is that the consumption of glucose as it is released by the enzymatic hydrolysis limits the risks of contamination.

DETAILED DESCRIPTION OF THE INVENTION

The simultaneous saccharification and propagation method according to the invention is applied to a pretreated biomass. Said biomass is a lignocellulosic material, in other words a material which contains lignocellulose. The lignocellulosic material can contain other constituents, such as cellulose-based material (cellulose, hemicellulose), and also fermentable or non-fermentable sugars, and pectins. In general, the lignocellulosic material is derived from plant material: stalks, leaves, shells, husks from plants, leaves, boughs or wood from trees. The lignocellulosic material can also be derived from herbaceous material, from agricultural residues, from forest residues, from solid municipal waste or from papermaking effluents.

According to one embodiment of the invention, the biomass used in the method is derived from *Miscanthus*, from poplar, or from wheat straw.

The lignocellulosic material must be pretreated in order to break the lignin and the crystalline structure of the cellulose. This facilitates the solubilization of the hemicellulose and of the cellulose and their accessibility for the enzymes that may be used in the treatment of the biomass. Any pretreatment means, in particular impregnation and then pretreatment means, known to those skilled in the art can be suitable. Schematically, the pretreatment can be chemical, mechanical or biological. The chemical pretreatment comprises treatment with a basic acid catalytic agent, in particular sulfuric acid, or with organic solvents, sulfur dioxide or carbon dioxide. Oxidation in a liquid medium and hydrothermolysis at controlled pH are also considered to be chemical treatments.

The mechanical pretreatment corresponds to any mechanical or physical treatment such as grinding, irradiation, high-pressure or high-temperature explosion (steam explosion). According to certain embodiments, the chemical and mechanical treatments can be combined, sequentially or simultaneously.

According to one advantageous embodiment, the pretreatment of the raw material comprises the following steps:
impregnation in the presence of an acid or basic chemical catalytic agent, in particular an acid catalyst, preferentially sulfuric acid, in proportions of between 0.1% and 2.0% by weight, preferentially 0.5%. Advantageously, said impregnation is carried out at a temperature of between approximately 50° C. and approximately 80° C., in particular of between approximately 60° C. and 70° C., preferentially at approximately 65° C.;
steam injection at a temperature of between approximately 120° C. and approximately 250° C., in particular of between approximately 170° C. and approximately 190° C., preferentially at approximately 180° C., at a pressure of between approximately 5 and approximately 15 bar, in particular of between approximately 8 and approximately 10 bar, preferentially at approximately 9 bar, and for a time of between 1 and 10 min, preferentially 5 min.

The pretreated plant biomass can then be used as a substrate for yeast propagation and/or in alcoholic fermentation, as indicated in FIG. 1 described above.

The propagation is also called multiplication, proliferation or production of biomass. The objective is to obtain an optimal amount of biomass for the fermentation. The propagation medium derived from the pretreated biomass can be rich in pentoses, rich in hexoses or a mixture of pentoses and hexoses. The term "pentoses" is intended to mean sugars having 5 carbon atoms, also called C5 sugars or more simply C5. The main natural monomeric representatives of pentoses are D-xylose and L-arabinose. By analogy, hexoses are sugars having 6 carbon atoms, also called C6 sugars or more simply C6. The main representatives of hexoses in monomeric form are glucose, fructose, mannose and galactose.

The SSP (simultaneous saccharification and propagation) propagation according to the present invention is aimed at yeasts, capable of converting both one or more pentoses and one or more hexoses.

The expression "yeast strain" denotes a homogeneous population of yeast cells. A yeast strain is obtained from the isolation of a clone. A clone gives rise to a cell population obtained from a single yeast cell.

The expression "derived yeast strain" denotes a yeast strain derived by one or more crosses and/or by mutation and/or by genetic transformation.

A yeast strain derived by crossing can be obtained by crossing which may or may not be interspecific. A yeast strain derived by mutation can be a yeast strain having undergone at least one spontaneous mutation in its genome or at least one mutagenesis-induced mutation. The mutation(s) of a derived strain may or may not affect the phenotype. The expression "mutagenesis" denotes the process of occurrence of a mutation. Conventionally, two methods are possible, random mutagenesis and insertional or site-directed mutagenesis. The first consists of the application of a physical treatment (for example UV radiation) or of a treatment with mutagenic chemical agents that will randomly induce mutations in the genome of the organism studied. The second will use molecular biology methods to bring about a precise modification (i.e. promoter, gene, terminator, etc.), either in any region of the genome, or on a precise locus. The term "locus" is intended to mean the precise and invariable physical position of a gene on a chromosome. A yeast strain derived by genetic transformation is a yeast strain into which has been introduced a DNA sequence which is preferably provided by a plasmid or directly integrated into the genome.

Schematically, it is possible to distinguish four phases during the propagation of a yeast strain: the "lag" phase during which no growth is detectable and which can be likened to an adaptation period; it is followed by the "growth phase" during which the cells multiply at the maximum growth rate, then the "stationary phase" into which the fermenting organism enters when the maximum growth period decreases and then stops, and, finally, the decline phase during which the number of viable cells will decrease. Propagation is generally an aerated process. Aerobiosis, or aeration of the propagation medium, guarantees a much better biomass production yield than anaerobiosis. Likewise, nutrients can be introduced into the medium, such as a nitrogen source, a phosphorus source or minerals. Vitamins and organic compounds such as amino acids or nucleic acids are rarely added in industry because of their cost. The faster and shorter the growth phase, the more the microbial contaminations will be avoided. An excessively high contamination of the propagation will result in production yield losses during the subsequent fermentation step. In order to limit the contaminations, antimicrobial agents and antibiotics of penicillin or virginiamycin type, or acid extracts of hops, can be used.

The propagation by SSP according to the invention must be carried out in microaerobiosis. This means that the medium is aerated but the amount of oxygen provided is limiting. The dissolved oxygen pressure is zero, contrary to aerobiosis. The dissolved oxygen in the fermentation medium is measured using an oxygen probe according to a method known to those skilled in the art. The microaerobiosis in the method according to the invention is obtained by moderate aeration and stirring. Preferentially, the aeration is 0.1 VVM (volume of air/volume of medium/minute, that is to say 60 ml for a reactor containing 600 ml of medium and per minute) and the stirring is set at around 500 rpm. Concretely, the stirring depends on the scale on which the method is carried out; in other words, those skilled in the art adjust according to the material, the volume of said material, and the acceptable energy expenditure. The higher the working volume, the weaker the stirring.

The biomass obtained can then be used in a fermentation process. The fermentation is preferably carried out at 32° C., with moderate stirring, for example 90 rpm. The stirring is moderated so as not to be oxygenating. The pH of the fermentation medium is preferably controlled, for example by the buffering capacity of an acid/base pair. The preferred target pH in the method according to the invention is 5.0. When the objective of the fermentation is to produce ethanol, the amount of ethanol present in the fermentation medium is measured by any suitable means known to those skilled in the art. It may be a direct measurement of the ethanol produced or an indirect measurement via a parameter that correlates with the ethanol production, such as the loss of mass. For example, the ethanol production can be measured by chromatography, in particular by HPLC (High Performance Liquid Chromatography), using an enzymatic kit, or by means of an assay with potassium dichromate. The amount of xylose and/or of glucose present in the medium is measured by any suitable means known to those skilled in the art, preferably by chromatography, in particular by HPLC.

Those skilled in the art know how to determine the appropriate conditions for an alcoholic fermentation.

By way of example, reference may be made to the alcoholic fermentation conditions described in the reference book "Yeast Technology", 2nd edition, 1991, G. Reed and T. W. Nagodawithana, published by Van Nostrand Reinhold, ISBN 0-442-31892-8.

The fermentation medium comprises the following elements: at least one fermentable carbon source, at least one nitrogen source, at least one sulfur source, at least one phosphorus source, at least one vitamin source and/or at least one mineral source.

The carbon source is for example provided in the form of a sugar that can be immediately assimilated by the yeast, such as xylose, arabinose, glucose, fructose or galactose, a disaccharide of saccharose type and/or a mixture of these sugars.

These sugars can be provided in the form of syrup, of molasses, of EP2 (low-grade run-off from the 2nd crystallization of the sugar), of hydrolysates of all or part of a plant material and/or of a mixture thereof.

The nitrogen source is for example provided in the form of yeast extracts, of ammonium sulfate, ammonium hydroxide, diammonium phosphate, aqueous ammonium, urea and/or a combination thereof.

The sulfur source is for example provided in the form of ammonium sulfate, magnesium sulfate, sulfuric acid and/or a combination thereof.

The phosphorus source is for example provided in the form of phosphoric acid, potassium phosphate, diammonium phosphate, monoammonium phosphate, and/or a combination thereof.

The vitamin source is for example provided in the form of corn steep liquor, molasses, yeast hydrolysate, a solution of pure vitamin or of a mixture of pure vitamins, and/or a combination thereof. The vitamin source provides the yeast with all of the vitamins in amounts that are at least equivalent to those recommended in the reference handbooks. Several vitamin sources can be combined.

The mineral source is for example provided in the form of molasses, a mixture of mineral salts and/or a combination thereof.

The mineral source provides the yeast with all of the macroelements and trace elements in amounts that are at least equivalent to those recommended in the reference handbooks. Several mineral sources can be combined.

One and the same substance can provide several different elements.

The propagation according to the invention is characterized in that the saccharification and the propagation are carried out simultaneously.

The raw pretreated marc is used in a proportion of a solids content of between 8% and 15%, preferentially between 10% and 12%, advantageously at 10%. According to one embodiment of the invention, the marc comprises approximately ⅓ of soluble solids (of "C5 liquor" type) and ⅔ of insoluble solids (of lignocellulosic fiber type).

The raw pretreated marc is brought into contact with a population of yeasts capable of metabolizing pentoses and hexoses. The yeasts are added, preferentially in dry form, in a proportion of 0.2 to 2 g/kg, in other words in a proportion of 0.2 to 2 g of yeast dry matter per kilogram of prepared complete medium.

A combination of cellulases and hemicellulases which enable the saccharification is added to the mixture of raw pretreated marc and yeasts. The saccharification corresponds to the hydrolysis of the polysaccharides into soluble monomer sugars. This means that the concentration of simple sugars would increase in the medium if they were not consumed by the yeasts for the propagation, in parallel to their release by the enzymes. The cells thus enable the hydrolysis of the cellulose so as to obtain glucose. The exocellulases or cellobiohydrolases act at the ends of the cellulose to form the disaccharide cellobiose. The endoglucanases act by cleavage of the internal bonds of the cellulose, forming cellulose-based oligosaccharides. The cellobiases or beta-glucosidases hydrolyze the cellulose-based oligopolymers and the cellobiose via their reducing end, releasing glucose.

Concretely, the term "cellulases" groups together a mixture of enzymatic proteins. Preferentially, the enzymes are used in a proportion of 5 to 15 mg of proteins (enzymes) per gram of solids. Advantageously, they are used in a proportion of 7 to 10 mg of proteins (enzymes) per gram of solids, preferentially 7 mg of enzymatic proteins per gram of solids. In order to enable correct understanding and a comparison between the activities of various compositions having cellulase-type activity, the FPU (Filter Paper Unit) activity can be used as a reference. The biotechnology commission of the international organization IUPAC (International Union of Pure and Applied Chemistry) recommends the following procedure: the FPU activity is measured on Whatman No. 1 paper at the initial concentration of 50 g.l$^{-1}$. The aim is to determine, by colorimetric assay (with dinitrosalicylic acid, DNS), the amount of reduced sugars derived from the Whatman No. 1 paper. By way of example, the test sample of the enzymatic solution to be analyzed that releases the equivalent of 2 g.l$^{-1}$ of glucose in 60 minutes is determined. The specific activities are obtained by dividing the activities, expressed in IU.ml$^{-1}$, by the protein concentration; they are expressed in IU.mg$^{-1}$.

Advantageously, the combination of cellulases and hemicellulases used in a method according to the invention corresponds to an enzymatic composition having one or more improved activities compared with a composition containing proteins produced by the native fungus. Such cellulases are known to those skilled in the art, for example described by Durand et al., 1988 (Enzyme Microb. Technol., 10: 341-346). According to one preferred embodiment of the invention, the cellulases correspond to an enzymatic composition as described in application WO 2010/029259 A1, in particular an enzymatic composition produced by filamentous fungi, preferentially *Trichoderma reesei*.

The mixture is then incubated, in microaerobiosis, at a temperature of between 25 and 38° C., preferentially between 28 and 33° C., preferentially between 30 and 32° C.

Advantageously, the pH of the solution is around 5.0.

The incubation is maintained between 24 and 50 hours, particularly between 28 and 50 hours, more preferentially between 30 and 42 hours.

Advantageously, the target cell concentration (at the end of propagation) is between 5.0×10$^8$ and 1.0×10$^9$ cells per milliliter.

According to one particular embodiment of the invention, the transformed yeasts capable of metabolizing both pentoses and hexoses are obtained according to methods described in patent applications WO 2010/000464 A1, WO 2011/128552 A1 and WO 2012/072793 A1. Advantageously, said strains are also resistant to acetic acid, obtained according to a method as described in application WO 2013/178915 A1.

According to one embodiment of the invention, the yeast strain used preferentially metabolizes xylose and glucose. In other words, according to one particular embodiment, the invention relates to a method for fermenting sugars derived from lignocellulosic biomass, preferentially pentoses and/or hexoses, using a fermenting microorganism, characterized in that said microorganism was produced directly on raw pretreated marc, according to a simultaneous saccharification and propagation method.

According to one preferred embodiment of the invention, the yeast strain subjected to simultaneous saccharification and propagation according to the invention corresponds to one of the strains deposited with the CNCM (Collection Nationale de Cultures de Microorganismes [French National Collection of Microorganism Cultures], Institut Pasteur, 25 rue du Docteur Roux, 75724 Paris Cedex 15) on May 24, 2012, under numbers I-4624, I-4625, I-4626 and I-4627 or to the strain deposited on Jun. 26, 2013, under number I-4783.

According to one preferred embodiment of the invention, the propagation by SSP precedes a fermentation step.

Another subject of the present invention is a method for producing at least one fermentation product, comprising a fermentation step, under anaerobic or semi-aerobic conditions, by a yeast propagated on raw pretreated marc according to a method in which the saccharification and the propagation are carried out simultaneously.

The fermentation product is in particular chosen from ethanol, a metabolite obtained from ethanol, or a secondary metabolite.

A preferred fermentation product according to the invention is ethanol.

The invention can be better understood in the light of the following examples which are in no way limiting.

EXAMPLE 1

Conditions for Pretreatment and Analysis of the Composition of the Substrate

The substrate used in these tests is raw wheat straw marc obtained using a pretreatment according to the following method: the ground straw is impregnated in acid water containing between 0.1% and 2.0% by weight of $H_2SO_4$, then pretreated by continuous steam explosion at approximately 50% of solids for 1 to 10 min between 170 and 190° C., preferentially at 180° C.

This raw straw marc was analyzed by high performance liquid chromatography (HPLC) and the sugar and inhibitor contents are indicated in table 1.

TABLE 1

Composition of the straw marc used for the present study
Concentrations in g/kg

|  | Raw marc concentrations in g/kg |
|---|---|
| Solids Content (SC) (%) | 46.02% |
| Sugars | |
| Cellulose | 170 |
| Cellobiose | 4 |
| Glucose | 9.7 |

TABLE 1-continued

Composition of the straw marc used for the present study
Concentrations in g/kg

|  | Raw marc concentrations in g/kg |
|---|---|
| Xylose | 93.8 |
| Galactose | NQ |
| Arabinose | 10.9 |
| Mannose | 2.1 |
| Inhibitor compounds | |
| Lactic acid | 0.7 |
| Acetic acid | 3.6 |
| Formic acid | 0.6 |
| 5-HMF | 0.4 |
| Furfural | 0.2 |

NQ means not quantified, in other words not measured.

The analysis of the substrates showed conventional acetic acid and furfural contents. The solids content of the raw straw marc is equal to 46.0%. In most of the propagation tests subsequently carried out, said marc was used at 10% solids, which corresponds to a 4.6-fold dilution of the concentrations given above during the processing in the reactor, while the other two substrates presented in the table, namely the hydrolysate and the C5 liquor, were used without additional dilution.

The following experiments were carried out with the *Saccharomyces cerevisiae* yeast deposited with the CNCM (Collection Nationale de Cultures de Microorganismes, Institut Pasteur, 25 rue du Docteur Roux, 75724 Paris Cedex 15) on Jun. 26, 2013, under number I-4783. The methods used are described hereinafter. By way of comparison, another yeast strain capable of metabolizing pentoses and hexoses would give similar results.

The reference methods use liquid substrates, namely lignocellulosic hydrolysate, which requires a step of hydrolysis of the pretreated marc prior to the propagation, or C5 liquor, (also called hemicellulosic hydrolysate), which requires a step of separation of the soluble sugars from the marc at the pretreatment output.

Conversely, the simultaneous saccharification and propagation (SSP) protocol according to the invention uses the solid substrate of raw pretreated marc.

EXAMPLE 2

Reference Methods 2.1. Protocols

Antibacterial agents and nutrients were added respectively to the C5 liquor and to the lignocellulosic hydrolysate according to amounts adapted to the yeast deposited with the CNCM under number I-4783 used in these tests, namely:

25% NH$_4$OH

Urea

85% H$_3$PO$_4$

Mineral mixture

Antibacterial agent

The composition of the mineral mixture is presented in table 2. Those skilled in the art will know how to adjust the proportions for optimal efficiency.

TABLE 2

Composition of the mineral mixture
Compound

MgSO$_4$•7H$_2$O
CuSO$_4$•2H$_2$O
MnCl$_2$•4H$_2$O
ZnSO$_4$•7H$_2$O

The reactors were inoculated in a proportion of 0.4 g/kg of dry yeast, and maintained at a temperature of 30° C.

The pH was maintained at 5.0 by adding KOH and H$_2$SO$_4$.

For the microaerobiosis conditions, the air flow rate was set at 0.1 VVM (volume of air/volume of medium/minute) and the stirring was set at 500 rpm.

By way of indication, an air flow rate of 0.1 VVM is 60 ml/min for a reactor containing 600 ml of medium.

2.2. Results 2.2.1. Propagation on Lignocellulosic Hydrolysate (SHF)

The kinetics of yeast growth, of substrate consumption and of ethanol production during the yeast propagation under microaerobic conditions (0.1 VVM) on the lignocellulosic hydrolysate are presented in FIG. 2.

This propagation test lasted 46.1 h, but FIG. 2 shows that the growth of the yeasts was finished after approximately 27 h of culture. The final content of biomass produced is estimated at $3.9 \times 10^8$ cells/ml. The glucose was consumed preferentially to the xylose, as is commonly the case where there is an excess of glucose. 18 g/kg of ethanol were produced.

Observation: The viability of the yeasts during the propagation is not represented on the figure in the interests of easier readability. Once the first hours of culture have passed, it is greater than 95% for all the tests presented in these examples.

2.2.2. Propagation on C5 Liquor

The kinetics of yeast growth, of substrate consumption and of ethanol production during the yeast propagation under microaerobic conditions (0.1 VVM) on C5 liquor are presented in FIG. 3.

This propagation test on C5 liquor shows a longer lag phase (than that of the test on lignocellulosic hydrolysate), and then the biomass rapidly increases to reach $7.5 \times 10^8$ cells/ml after 41 h of culture. 10 g/kg of ethanol were produced.

The difference in final content of biomass has already been observed. In general, the yeast production yields are higher during propagation on C5 liquor than in propagation on lignocellulosic hydrolysate, mainly composed of C6 sugar (glucose).

EXAMPLE 3

Simultaneous Saccharification and Propagation (SSP)

3.1. SSP Method According to the Invention

The simultaneous saccharification and propagation method is also carried out in a reactor comprising:

water, cellulose-based raw pretreated marc (solid substrate) used in a proportion respectively of 10% or 12% of solids (SC) in most of the tests, and nutrients as indicated above for the reference methods.

The propagation was initiated by the simultaneous addition of cellulases (in a proportion respectively of 7 and 10 mg of proteins per gram of SC) and of the dry yeast in a proportion of 0.4 g/kg.

The enzymes used in the present examples can be replaced with commercial enzymes in equivalent amount. By way of comparison, the FPase activity (see above, the reference to Filter Paper Units) specific for the cellulases used in the examples is between 0.8 and 1.5 IU.mg$^{-1}$. They can be replaced with commercial enzymes in the same amounts (in IU.mg$^{-1}$).

The temperature was maintained respectively at 30° C. or 32° C.

The pH was maintained at 5.0 by adding KOH and $H_2SO_4$.

For the microaerobiosis conditions, the air flow rate was set at 0.1 VVM (volume of air/volume of medium/minute) and the stirring was set at 500 rpm.

Samples were taken during the various propagation tests, in order to count the yeasts and to quantify the sugars and the fermentation products by high performance liquid chromatography (HPLC).

Total enzymatic hydrolyses were carried out on the final samples so as to determine the content of non-hydrolyzed cellulose at the end of propagation.

3.2. Solids Content (SC)-Enzyme Dose Pairs

Various SC-enzyme dose pairs were tested in SSP. The prerequisites were: (i) a fermentable sugar concentration which must make it possible to achieve a biomass content of about 15 g/kg at the end of propagation; (ii) cellulose hydrolysis kinetics which must limit the amount of glucose, such that (1) the carbon stream is directed toward the production of biomass rather than toward the production of ethanol, which could happen, even in the presence of oxygen, if the sugar concentration is too high, and that (2) the use of xylose is favored without the productivity being penalized; and (iii) the viscosity of the mixture must allow moderate stirring and microaeration of the medium.

The solids contents (SC) and the enzyme doses tested are indicated in table 3.

TABLE 3

Solids contents (SC) and enzyme doses tested in SSP

| Test | Solids content (SC) % | Enzyme dose mg prot./g SC |
| --- | --- | --- |
| 1 | 10 | 10 |
| 2 | 12 | 10 |
| 3 | 10 | 7 |

Reminder: as for the reference methods (above), these propagation tests were inoculated with 0.4 g/kg of dry yeast, then carried out at pH 5.0, at 30° C., with moderate stirring at 500 rpm and microaeration of 0.1 VVM.

3.2.1. Propagation in SSP at 10% of SC and 10 mg Enzymatic Proteins/g of SC

The I-4783 yeast was subjected to propagation under microaerobic conditions (0.1 VVM) on the raw straw marc (at 10% SC), in the presence of cellulases (10 mg proteins/g of SC) which make it possible to simultaneously carry out the hydrolysis of the cellulose. The kinetics of yeast growth and of ethanol production, and also the change in the glucose and xylose concentrations, during the yeast propagation are represented in FIG. 4.

Result: this propagation test lasted 41 h, at the end of which 5.6×10$^8$ cells/ml were obtained. 11 g/kg of ethanol were produced, then partially consumed during this propagation in SSP on raw straw marc. Moreover, the solids content (SC) used made it possible to add all of the substrate to the initial vessel heel while at the same time retaining a low viscosity allowing moderate stirring and microaeration of the culture medium.

The experiment was repeated with the growth being extended beyond 41 h. The results (not shown) were the following: 6.5×10$^8$ cells/ml were obtained after 48 h of culture and the growth kinetics were superimposed on those previously obtained under the same operating conditions.

3.2.2. Propagation in SSP at 12% of SC and 10 mg Enzymatic Proteins/g of SC

The I-4783 yeast was subjected to propagation under microaerobic conditions (0.1 VVM) on the raw straw marc (at 12% of SC), in the presence of cellulases (10 mg proteins/g of SC) which make it possible to simultaneously carry out the hydrolysis of the cellulose. The kinetics of yeast growth and of ethanol production, and also the change in the glucose and xylose concentrations, during the yeast propagation are represented in FIG. 5.

Result: this propagation test lasted 46.3 h, at the end of which 5.8×10$^8$ cells/ml were obtained. 15 g/kg of ethanol were produced, then partially consumed during this propagation in SSP on raw straw marc.

The increase in the solids content (SC) from 10% to 12% did not cause any significant increase in the viscosity capable of disrupting the moderate stirring and the microaeration of the culture medium.

3.2.3. Propagation in SSP at 10% of SC and 7 mg Enzymatic Proteins/g of SC

The I-4783 yeast was subjected to propagation under microaerobic conditions (0.1 VVM) on the raw straw marc (at 10% SC), in the presence of cellulases (7 mg enzymatic proteins/g of SC) which make it possible to simultaneously carry out the hydrolysis of the cellulose. The kinetics of yeast growth and of ethanol production, and also the change in the glucose and xylose concentrations, during the yeast propagation are represented in FIG. 6.

Result: this propagation test lasted 43.9 h, at the end of which 8.3×10$^8$ cells/ml were obtained. 9.3 g/kg of ethanol were produced, then totally consumed during this propagation in SSP on raw straw marc.

Discussion

Comparison of the performance levels obtained for the SSP tests carried out at various SCs and enzyme doses show that:

The increase in the SC from 10 to 12% for the tests carried out with 10 mg of proteins/kg SC leads to an increase in ethanol production, but does not have a positive impact on the yeast growth.

The decrease in the enzyme dose from 10 to 7 mg of enzymatic proteins/g SC for the tests carried out at 10% SC leads to a greater glucose limitation which results in a faster consumption of xylose and a carbon stream more directed toward the biomass production. The difference in hydrolysis yield due to the decrease in the enzyme dose is less than 2% at the end of propagation.

3.3. Effect of the Temperature

With the aim of observing the effect of the temperature on the efficiency of the propagation in SSP, the I-4783 yeast was propagated at 32° C. under microaerobic conditions (0.1 VVM) on the raw straw marc (in a proportion of 10% of SC) in the presence of cellulases (in a proportion of 10 mg proteins/g of SC). The kinetics of yeast growth and of ethanol production, and also the change in the glucose and xylose concentrations, during this propagation test are represented in FIG. 7.

Result: this propagation test lasted 42.6 h. A slowing of growth was observed at the end of culture. 12 g/kg of ethanol were produced, then partially consumed. The final biomass was estimated at $5.7 \times 10^8$ cells/ml.

FIG. 8 compares the change in the yeast population, and also the change in the xylose and ethanol concentrations, for the SSP tests carried out respectively at 30° C. and 32° C., at 10% of SC and 10 mg proteins/g SC.

No positive effect was observed on the yeast growth.

It appears that the increase in temperature can promote the uptake of the xylose, which results in faster ethanol production kinetics.

The increase in the temperature improves the enzymatic hydrolysis and increases the amount of fermentable sugars (by 12% in this case). If the propagation must is entirely transferred in order to inoculate the alcoholic fermentations, the residual sugars, regardless of their form, represent a small proportion and will be using during the alcoholic fermentation.

3.4. Method Robustness Test: SSP Test in the Presence of a High Concentration of Acetate With the aim of evaluating the robustness of the SSP method, tests were carried out with addition of acetate to the medium (QS (quantity sufficient) for 3 g/kg) in order to simulate a higher toxicity of the pretreated marc. These tests were carried out at pH 5.0, 30° C., with 10% of SC and enzyme/substrate ratios equal to 7 mg proteins/g of SC and 10 mg proteins/g of SC. The increase in the acetate content in the culture medium from 0.7 g/kg to 3 g/kg corresponds to an increase in the acetic acid content of the pretreated marc from 3.6 g/kg to 13.8 g/kg.

The latter concentration leaves a considerable margin for the increase in the volatile compound content of the pretreated substrates when passing to the industrial scale.

The yeast growth kinetics, and also the change in xylose and ethanol concentrations, during the propagation tests carried out with and without addition of acetate, at 10% of SC and 7 mg proteins/g of SC are illustrated in FIG. 9.

Comparison of the SSP kinetics carried out respectively in the presence of 0.7 g/kg or 3.0 g/kg of acetic acid shows that the increase in acetate concentration slows down the use of xylose and causes a visible delay in growth up to 25 h of culture. The carbon stream is slightly diverted toward ethanol production. However, the difference in biomass concentration disappears at the end of culture: $8.0 \times 10^8$ cells/ml were obtained in 42.5 h for the test at 3.0 g/kg of acetate, whereas $8.3 \times 10^8$ cells/ml were obtained in 43.9 h for the test at 0.7 g/kg of acetate.

The yeast growth kinetics, and also the change in xylose and ethanol concentrations, during the propagation tests carried out with and without addition of acetate, at 10% of SC and 10 mg proteins/g of SC are illustrated in FIG. 10.

Comparison of the SSP kinetics carried out respectively in the presence of 0.7 g/kg or 3.0 g/kg of acetic acid shows that the increase in acetate concentration causes a visible delay in growth up to 30 h of culture and that the carbon stream is slightly diverted toward ethanol production. At the end of propagation, the biomass content produced in the presence of 3 g/kg of acetate exceeds the reference: $6.9 \times 10^8$ cells/ml were obtained in 46.7 h compared with $6.5 \times 10^8$ cells/ml in 48.1 h for the test without addition of acetate.

These results show that the considerable increase in the amount of acetic acid in the pretreated straw marc does not significantly degrade the performance levels of the method of propagation in SSP. Such a robustness cannot be expected of the method of yeast propagation on C5 liquor, since the xylose fermentation is much more strongly affected than the glucose fermentation by the toxicity of the culture medium.

Here again, two enzyme/substrate ratios were tested. The results are consistent with those previously obtained (above), namely that the decrease in the enzyme dose improves the performance levels of the SSP method.

EXAMPLE 4

Comparison of the Growth Performance Levels of the SSP According to the Invention with Those Obtained with the Reference Methods The change in the yeast population is compared with that obtained for the reference methods, under temperature, pH, microaeration, moderate stirring and inoculation level conditions that are identical. The amounts of fermentable sugars are of the same order of magnitude.

4.1. Comparison with the Propagation on the Lignocellulosic Hydrolysate (SHF)

The change in the yeast population during the propagation on lignocellulosic hydrolysate and the SSP tests, with and without addition of acetate, at 10% of SC and 7 mg proteins/g of SC is represented in FIG. 11.

Result and Discussion

The respective substrates of the test for propagation on lignocellulosic hydrolysate and of the SSP propagation test without addition of acetate are identical, except for one difference: one was hydrolyzed beforehand. The growth is slower on the hydrolysate, this being the case from the beginning of the propagation, which can be explained by a slightly higher acetate content due to the more extensive hydrolysis of the substrate at the beginning of culture (1.0 g/kg compared with 0.7 g/kg in SSP); the osmotic pressure due to the sugars is also higher. In addition to its better kinetics, the propagation in SSP makes it possible to obtain a much greater amount of biomass ($8.3 \times 10^8$ cells/ml compared with $3.9 \times 10^8$ cells/ml).

In addition, it is surprising to note that the SSP propagation test carried out in the presence of 3 g/kg of acetate is also better than the reference test.

4.2. Comparison with the Propagation on C5 Liquor

The change in the yeast population during the propagation on C5 liquor and the SSP tests, with and without addition of acetate, at 10% of SC and 7 mg enzymatic proteins/g of SC is represented in FIG. 12.

Result and Discussion

The propagation carried out on C5 liquor has growth kinetics that are significantly slower than the SSP propagation tests on raw marc; however, the increase in growth rate at the end of propagation allows it to achieve a final biomass content equivalent to the SSP propagations. However, if the propagation time was reduced compared with the test presented, the advantage of the SSP propagation with respect to the propagation on C5 liquor would increase.

The C5 liquor used for this propagation test was derived from the same cellulosic wheat straw marc as that used for the SSP propagation tests. It was obtained by suspending the cellulose-based marc in water, followed by solid/liquid separation. This method for obtaining the C5 liquors in reality extracts all the soluble elements from the pretreated marc; it can therefore be considered and it was verified that the inhibitor content is proportional to the xylose concentration, which makes the C5 liquor the most concentrated substrate in terms of inhibitors.

Moreover, the fact that the xylose uptake is affected to a greater extent by the toxicity of the medium than the glucose consumption and that the increase in the toxicity of the pretreated marc leads to a faster increase in inhibitor content in the C5 liquor (since it is proportional to the xylose content) means that the advantage of the SSP method will increase as the toxicity of the pretreated marc increases. Thus, the increase in acetate content from 0.7 g/kg to 3.0 g/kg in the vessel heel of the SSP, which slightly degrades the growth kinetics in SSP, corresponds to an increase in the acetate content from 1.6 g/kg to approximately 7 g/kg in the C5 liquor, which greatly penalizes the yeast growth.

4.3. Synthesis and Comparison of the Propagation Performance Levels

Table 4 provides, for each propagation test carried out:
the sugar concentration used in the culture medium (total amount and fermentable amount for the tests carried out in SSP),
the final concentration of biomass obtained (in cells/ml),
the biomass production yield (related back to the fermentable sugar content and related back to the SC content),
an estimation of the yeast production yield in g of yeast/g of fermentable sugars.

TABLE 4

Amount of sugars used, biomass concentrations obtained and biomass production yields for the various propagation tests (cell means cells, mass ini. and mass fin. mean respectively initial mass and final mass).

| Conditions | Time h | Sugar potential g/kg | Fermentable sugars g/kg | Final biomass Cell/ml | Mass ini. g | Mass fin. g | Yield Cell/g fermentable sugars | Yield g yeast/ g sugars |
|---|---|---|---|---|---|---|---|---|
| C5 liquor, 30° C. | 41 | | 53.8 | 7.50E+08 | 600 | 607.4 | 1.41E+10 | 0.29 |
| SHF, 10% SC, 30° C. | 46.1 | | 65.6 | 3.90E+08 | 600 | 593.7 | 5.88E+09 | 0.12 |
| 10% SC, 10 mg prot/g SC, 30° C. | 41 | 64.5 | 53.3 | 5.60E+08 | 600 | 523.0 | 9.16E+09 | 0.19 |
| 10% SC, 10 mg prot/g SC, 30° C. | 48.1 | 64.5 | 53.3 | 6.50E+08 | 600 | 557.0 | 1.13E+10 | 0.24 |
| 10% SC, 10 mg prot/g SC, 32° C. | 42.6 | 64.5 | 59.9 | 5.70E+08 | 600 | 616.3 | 9.78E+09 | 0.20 |
| 10% SC, 7 mg prot/g SC, 30° C. | 43.9 | 64.5 | 52.25 | 8.30E+08 | 600 | 604.9 | 1.60E+10 | 0.33 |
| 12% SC, 10 mg prot/g SC, 30° C. | 46.3 | 77.3 | 66.0 | 5.80E+08 | 600 | 571.5 | 8.37E+09 | 0.17 |
| 10% SC, 7 mg prot/g SC, 30° C., 3 g/kg of acetate | 42.5 | 64.5 | 52.25 | 8.00E+08 | 600 | 599.3 | 1.53E+10 | 0.32 |
| 10% SC, 10 mg prot/g SC, 30° C., 3 g/kg of acetate | 46.7 | 64.5 | 58.7 | 6.90E+08 | 600 | 610.4 | 1.20E+10 | 0.25 |

Observations:
The sugar potential is calculated on the basis of the hypothesis of a cellulose hydrolysis yield equal to 100%.
The amount of fermentable sugars is calculated by virtue of the estimation of the amount of residual cellulose by total enzymatic hydrolysis on a sample taken at the end of culture.
For the estimation of the biomass production yield in g of yeast/g of fermentable sugars, the conversion is carried out by considering that 1 g of yeast contains $4.8 \times 10^{10}$ cells (measured at the end of propagation on C5 liquor).
The final mass measured is abnormally low for the propagation tests carried out at 10% of SC with 10 mg of proteins at 30° C., which penalizes them when the yields are calculated.

Results and Discussion

Table 4 shows that the highest final concentration of biomass was obtained with the SSP method carried out at 10% of SC and 7 mg of protein/g of SC. The final biomass content obtained on the C5 liquor is close to that obtained with the SSP method under the best conditions, whereas the propagation on lignocellulosic hydrolysate results in a final biomass content that is significantly lower than all the other tests.

The calculation of the yeast production yield equals $1.6 \times 10^{10}$ cells/g of fermentable sugars for the most effective test carried out in SSP with 10% of SC and 7 mg of protein/g of SC at 30° C. (and $1.5 \times 10^{10}$ cells/g of fermentable sugars for the test carried out with an increased acetic acid concentration). The yield of the propagation on C5 liquor is slightly lower: $1.4 \times 10^{10}$ cells/g of fermentable sugars were obtained. The other SSP conditions tested show yeast production yields close to $1.0 \times 10^{10}$ cells/g of fermentable sugars, whereas the reference test carried out on lignocellulosic hydrolysate shows a yield of $5.9 \times 10^{9}$ cells/g of fermentable sugars, that is to say approximately 3 times less than the most effective SSP test.

In order to compare with known references, the biomass yield is estimated in g of yeast/g of fermentable sugar by taking into consideration a conversion: number of cells/g of SC obtained at the end of alcoholic propagation on C5 liquor. According to data known to those skilled in the art, the reference propagation on lignocellulosic hydrolysate has a yield of about 0.12 g/g.

The best SSP condition made it possible to obtain 0.33 g of yeast/g of fermentable sugars. The multiplication rate of the yeast in propagation is then greater than 40 (estimated final concentration 17.4 g/kg of yeast).

In terms of productivity, the method of propagation in SSP is also the most effective, indeed:
The average volume productivity is estimated at 0.38 g of yeast/kg of must/h for the SSP method, compared with respectively 0.37 g/kg/h and 0.17 g/kg/h for the propagations on C5 liquor and on lignocellulosic hydrolysate.
The average volume productivity over the first 30 hours of culture is estimated at 0.33 g of yeast/kg of must/h for the SSP method, compared with 0.26 g/kg/h for the propagations on C5 liquor and on lignocellulosic hydrolysate.

EXAMPLE 5

Validation of the SSP Propagation Method: Performance Levels of the Yeast Propagated in SSCF Fermentation The present invention is an essential intermediate link in an overall industrial process of alcoholic fermentation. The objective of the present example is to validate that the yeast obtained at the end of a propagation according to the invention is effective in alcoholic fermentation on lignocellulosic substrate.

The I-4783 yeast propagated in SSP was used to inoculate an SSCF (Simultaneous Saccharification and CoFermentation) fermentation; the two cultures were carried out on raw straw marc. The SSCF was carried out at 24% of SC with 10 mg of protein/g of SC, with addition of acetate to the medium (QS 4 g/kg). The reactor was inoculated with 2.4×10$^7$ cells/ml (i.e. about 0.5 g/kg of yeast) and the medium was maintained at pH 5.5 and 33° C. for 142.5 h. The change in the glucose, xylose and ethanol concentrations during this fermentation is illustrated in FIG. 13.

This SSCF fermentation exhibits kinetics consistent with what is usually obtained. The yeast very rapidly consumes the glucose released by the enzymes such that the glucose concentration is zero from the first hours of fermentation. The xylose released is predominantly consumed in 72 h; the ethanol production kinetics are then limited by the enzymatic hydrolysis. The final ethanol content is equal to 67.4 g/kg, which corresponds to a difference of less than 5% with the concentration obtained at the end of the SSCFs carried out without addition of acetate, with the I-4783 yeast propagated on C5 liquor. This result makes it possible to conclude that the propagation method according to the invention does not degrade the performance levels of the yeast produced compared with a propagation method on C5 liquor normally used.

The invention claimed is:

1. A method for propagating yeasts, for use in the production of a fermentation product from lignocellulosic biomass, consisting of the steps of:
   a. providing a reactor,
   b. placing in contact in said reactor:
      a population of yeasts capable of metabolizing pentoses and hexoses, in a proportion of from 0.2 to 2.0 g of yeast dry matter per kg of prepared complete medium, wherein the yeasts are from the yeast strain deposited with the CNCM on Jun. 26, 2013, under Accession Number I-4783,
      raw marc obtained from pretreatment of the lignocellulosic biomass at a solid content (SC) of between 8% and 15%, wherein said pretreatment does not include extraction and/or enzymatic hydrolysis, nutrients; and
      cellulases in a proportion of from 5 to 15 mg of protein per gram of SC,
   c. incubating the mixture at a temperature of between 25° C. and 38° C. in microaerobiosis,
wherein the saccharification of the raw marc and the growth of the yeasts are carried out simultaneously.

2. The propagating method as claimed in claim 1, wherein the pentoses are xylose and/or arabinose.

3. The propagating method as claimed in claim 1, wherein the hexose is glucose.

4. The propagating method as claimed in claim 1, wherein the incubation in step c. is maintained until a cell concentration between 5.0×10$^8$ and 1.0×10$^9$ cells per millilitre is obtained.

5. The propagating method as claimed in claim 1, wherein the yeasts are inoculated in a proportion of from 0.3 to 0.6 g/kg in the form of dry yeasts, the raw marc is used in a proportion of 10% of SC and the cellulases in a proportion of 7 mg of proteins per gram of SC, the aeration rate is set at 0.1 VVM, the temperature is set at 30° C. and the pH of the medium is set at pH 5.0.

6. The method according to claim 1, wherein in step c., the temperature is between 28° C. and 33° C.

7. A method for producing a fermented product from a lignocellulosic biomass, consisting of the steps of sequentially:
   a. pretreating the lignocellulosic biomass so as to obtain raw marc, wherein said pretreating step does not include extraction and/or enzymatic hydrolysis,
   b. bringing a fraction of the raw pretreated marc, in a proportion of from 10% to 12% of solids (SC), into contact with (i) a population of yeasts capable of metabolizing pentoses and hexoses, wherein the yeasts are from the yeast strain deposited with the CNCM, on Jun. 26, 2013, under Accession Number I-4783, (ii) cellulases in a proportion of from 5 to 15 mg of protein per gram of SC, and (iii) optionally, nutrients,
   c. incubating the mixture at a temperature of between 25° C. and 38° C. in microaerobiosis, so as to obtain propagated yeasts by simultaneous saccharification and propagation,
   d. transferring all or part of the propagated yeasts for bringing into contact with the fermentation must comprising a pentose source and a hexose source,
   e. carrying out the fermentation, under anaerobic or semi-aerobic conditions, and
   f. obtaining the fermented product.

8. The method as claimed in claim 7, wherein the lignocellulosic biomass is a biomass of plant origin.

9. The method as claimed in claim 7, wherein the fermented product obtained is ethanol.

10. The method according to claim 7, wherein in step c., the temperature is between 28° C. and 35° C.

11. The method according to claim 7, wherein the incubation in step c. is maintained until a cell concentration between 5.0×10$^8$ and 1.0×10$^9$ cells per millilitre is obtained.

* * * * *